(12) United States Patent
Drent et al.

(10) Patent No.: US 7,491,859 B2
(45) Date of Patent: Feb. 17, 2009

(54) PROCESS FOR THE TELOMERIZATION OF A CONJUGATED DIENE, CATALYST AND BIDENTATE LIGAND USEFUL THEREIN

(75) Inventors: Eit Drent, Amsterdam (NL); Michael Rolf Eberhard, Honolulu, HI (US); Paul Gerald Pringle, Bristol (GB); Renata Helena van der Made, Amsterdam (NL)

(73) Assignee: Shell Oil Company, Houston, TX (US)

( * ) Notice: Subject to any disclaimer, the term of this patent is extended or adjusted under 35 U.S.C. 154(b) by 419 days.

(21) Appl. No.: 11/299,101

(22) Filed: Dec. 9, 2005

(65) Prior Publication Data

US 2006/0084832 A1 Apr. 20, 2006

Related U.S. Application Data

(62) Division of application No. 10/882,932, filed on Jul. 1, 2004, now Pat. No. 7,057,082, which is a division of application No. 10/287,731, filed on Nov. 4, 2002, now Pat. No. 6,794,553.

(51) Int. Cl.
- *B01J 31/18* (2006.01)
- *B01J 31/22* (2006.01)
- *C07C 2/32* (2006.01)
- *C07C 2/36* (2006.01)

(52) U.S. Cl. .................. 585/514; 585/511; 502/162
(58) Field of Classification Search ................ 502/162; 585/511, 514
See application file for complete search history.

(56) References Cited

U.S. PATENT DOCUMENTS

| | | | | |
|---|---|---|---|---|
| 3,499,042 A | 3/1970 | Smutny | ...................... | 260/614 |
| 3,518,315 A | 6/1970 | Smutny | ...................... | 260/612 |
| 3,670,029 A | 6/1972 | Romanelli | ................... | 260/612 |
| 3,670,032 A | 6/1972 | Romanelli | ................... | 260/614 |
| 3,769,352 A | 10/1973 | Romanelli | ................... | 260/614 |
| 3,887,627 A | 6/1975 | Romanelli | ................... | 260/632 |
| 4,163,760 A | 8/1979 | Elsner et al. | .......... | 260/606.5 P |
| 4,196,135 A | 4/1980 | Enomoto et al. | ............ | 260/429 |
| 4,877,861 A * | 10/1989 | Van Doorn et al. | .......... | 528/392 |
| 5,254,782 A | 10/1993 | Schaart et al. | ............. | 585/509 |

FOREIGN PATENT DOCUMENTS

| | | |
|---|---|---|
| DE | 2040708 | 6/1971 |
| DE | 2703802 | 8/1978 |
| EP | 0218100 | 9/1986 |
| EP | 0311352 | 12/1989 |
| GB | 1178812 | 1/1970 |
| GB | 1301465 | 8/1970 |
| GB | 1248593 | 10/1971 |
| GB | 1354507 | 5/1974 |
| GB | 1561874 | 3/1980 |
| NL | 6816008 | 5/1969 |
| WO | WO 87/07600 | 12/1987 |
| WO | WO 91/00326 | 3/1991 |
| WO | WO 92/10450 | 6/1992 |
| WO | WO 00/09521 | 2/2000 |
| WO | WO 00/56695 | 9/2000 |

OTHER PUBLICATIONS

Chemical Abstracts, vol. 96, No. 25, Jun. 21, 1982 Columbus, Ohio, US; Abstract No. 217253, Kuraray Co., Ltd. Japan: "Telomerization of Butadiene and Isoprene" XP002244618.
Karsch H. H. et al., "Funktionelle Trimethylphosphanderivate, XVIII [1] Methyl(Phosphinomethyl)Silanes and -Stannanes," Zeitschrift Fur Naturforschung, Teil B: Anorganische Chemie, Organische Chemie., vol. 38b, No. 11, 1983, pp. 1399-1405 XP008018568.
Morimoto, T. et al., "A Convenient Method for the Synthesis of Bis(Trialkylphosphine)-Boranes Bearing Two Phospholanes," Synlett (1996), (12), pp. 1211-1212, 1996 XP002244948.

* cited by examiner

*Primary Examiner*—Caixia Lu
(74) *Attorney, Agent, or Firm*—Donald F. Haas

(57) ABSTRACT

Process for the telomerization of a conjugated diene, wherein the conjugated diene is reacted with a compound containing an active hydrogen atom and having a formula R'—H in the presence of a telomerization catalyst based on:
(a) a source of group VIII metal,
(b) a bidentate ligand
wherein the bidentate ligand has the general formula I $$R^1R^2M^1\text{-}R\text{-}M^2R^3R^4 \qquad (I)$$

wherein $M^1$ and $M^2$ are independently P, As or Sb; $R^1$, $R^2$, $R^3$ and $R^4$ independently represent a monovalent aliphatic group;
or $R^1$, $R^2$ and $M^1$ together and/or $R^3$, $R^4$ and $M^2$ together independently represent an optionally substituted aliphatic cyclic group with at least 5 ring atoms, of which one is the $M^1$ or $M^2$ atom, respectively;
R represents a bivalent organic bridging group; and novel bidentate diphosphines which can be used in this process.

1 Claim, 1 Drawing Sheet

US 7,491,859 B2

PROCESS FOR THE TELOMERIZATION OF A CONJUGATED DIENE, CATALYST AND BIDENTATE LIGAND USEFUL THEREIN

This is a division of application Ser. No. 10/882,932 filed Jul. 1, 2004, now U.S. Pat. No. 7,057,082, which is a division of application Ser. No. 10/287,731 filed Nov. 4, 2002, now U.S. Pat. No. 6,794,553, the entire disclosures of which are hereby incorporated by reference.

FIELD OF THE INVENTION

The present invention relates to a process for the telomerization of a conjugated diene, and a catalyst and bidentate ligand that can be used in this process.

BACKGROUND OF THE INVENTION

WO-A-9210450 describes a telomerization reaction wherein 1,3-butadiene is reacted with a compound containing an active hydrogen atom and having a formula R—H in the presence of a telomerization catalyst to form a 1-substituted-2,7-octadiene of formula $CH_2=CH-CH_2-CH_2-CH_2-CH=CH-CH_2-R$, in which R represent the residue of the compound containing an active hydrogen atom. WO-A-9210450 describes telomerization catalysts such as the transition metals Fe, Co, Ni, Ru, Rh, Pd, Os, Ir and Pt (Group VIII transition metals) and compounds thereof, including those supported on an inert carrier, as well as ligand compounds including diphosphines.

However, it is desirable to provide a process for the telomerization of a conjugated diene, wherein the telomerization reaction can be carried out with an improved selectivity towards the linear telomerization product.

SUMMARY OF THE INVENTION

Accordingly, a process for the telomerization of a conjugated diene is provided, comprising: reacting the conjugated diene with a compound containing an active hydrogen atom and having a formula R'—H in the presence of a telomerization catalyst based on:
(a) a source of group VIII metal,
(b) a bidentate ligand
wherein the bidentate ligand has the general formula I $$R^1R^2M^1\text{-}R\text{-}M^2R^3R^4 \qquad (I)$$

wherein $M^1$ and $M^2$ are independently P, As or Sb;
$R^1$, $R^2$, $R^3$ and $R^4$ independently represent a monovalent aliphatic group;
or $R^1$, $R^2$ and $M^1$ together and/or $R^3$, $R^4$ and $M^2$ together independently represent an optionally substituted aliphatic cyclic group with at least 5 ring atoms,
wherein one ring atom in said cyclic group is $M^1$ or $M^2$;
and R represents a bivalent organic bridging group.

In addition, a process for the preparation of 1-octene is provided, comprising:
a) reacting 1,3-butadiene with a compound containing an active hydrogen atom and having a formula R'—H in the presence of a telomerization catalyst based on:
(1) a source of group VIII metal,
(2) a bidentate ligand
wherein the bidentate ligand has the general formula I $$R^1R^2M^1\text{-}R\text{-}M^2R^3R^4 \qquad (I)$$

wherein $M^1$ and $M^2$ are independently P, As or Sb;
$R^1$, $R^2$, $R^3$ and $R^4$ independently represent a monovalent aliphatic group;
or $R^1$, $R^2$ and $M^1$ together and/or $R^3$, $R^4$ and $M^2$ together independently represent an optionally substituted aliphatic cyclic group with at least 5 ring atoms,
wherein one ring atom in said cyclic group is $M^1$ or $M^2$; and
R represents a bivalent organic bridging group; thereby producing 1-substituted-2,7-octadiene;
b) hydrogenating the 1-substituted-2,7-octadiene of step a), thereby producing 1-substituted octane;
c) decomposing the 1-substituted octane of step b), thereby producing 1-octene.

Also provided are catalyst systems and bidentate ligands useful in the processes of the present invention.

DETAILED DESCRIPTION OF THE INVENTION

Figure 1:
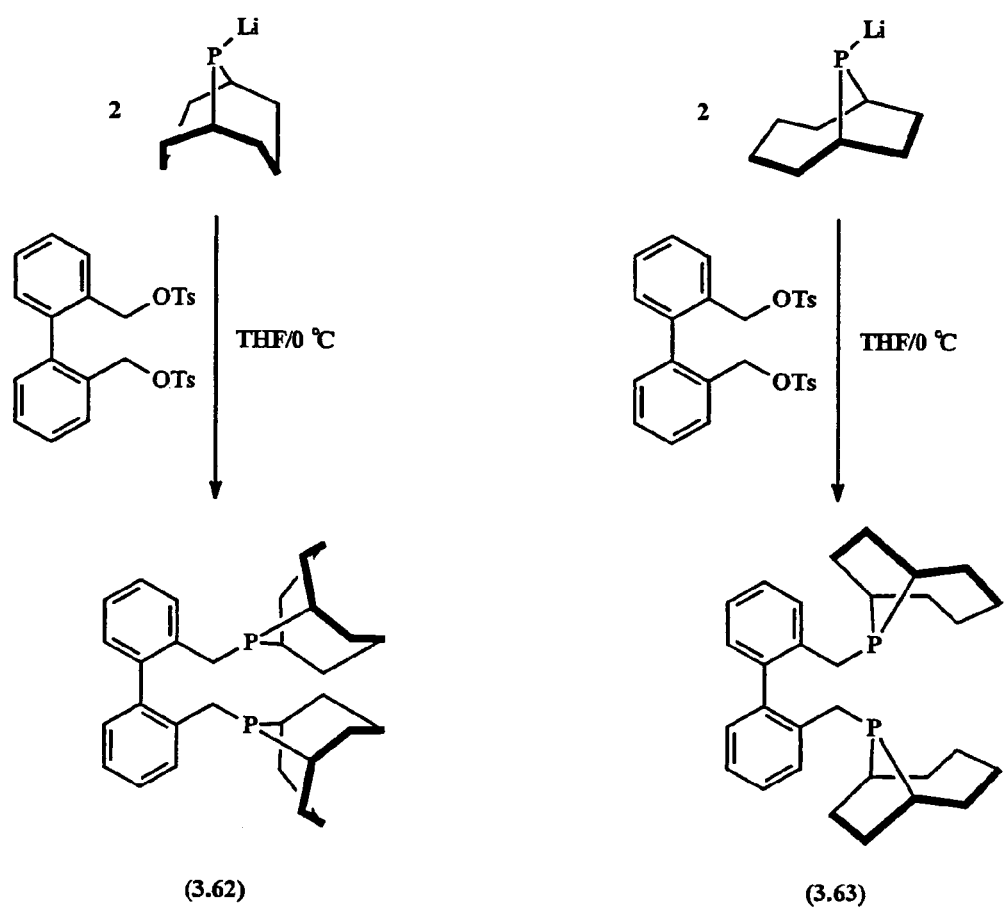
FIG. 1 illustrates examples of one embodiment of the preparation of ligands.

It has now been found that the telomerization of a conjugated diene can be carried out with a high selectivity towards the linear telomerization product in the presence of a specific catalyst system.

Accordingly, one embodiment of the present invention provides a process for the telomerization of a conjugated diene, wherein the conjugated diene is reacted with a compound containing an active hydrogen atom and having a formula R'—H in the presence of a telomerization catalyst based on:
(a) a source of group VIII metal,
(b) a bidentate ligand
wherein the bidentate ligand has the general formula I $$R^1R^2M^1\text{-}R\text{-}M^2R^3R^4 \qquad (I)$$

wherein $M^1$ and $M^2$ are independently P, As or Sb;
$R^1$, $R^2$, $R^3$ and $R^4$ independently represent a monovalent aliphatic group;
or $R^1$, $R^2$ and $M^1$ together and/or $R^3$, $R^4$ and $M^2$ together independently represent an optionally substituted aliphatic cyclic group with at least 5 ring atoms, of which one is the $M^1$ or $M^2$ atom, respectively;
and R represents a bivalent organic bridging group.

It has been found that the use of this specific catalyst system results in an improved selectivity towards the linear product whilst obtaining reaction rates well over 500 mol conjugated diene/mol group VIII metal/hour.

The conjugated diene preferably is a conjugated diene having from 4 to 20, more preferably from 4 to 8 carbon atoms per molecule. The conjugated diene may be substituted or unsubstituted, and may contain a number of heteroatoms. Examples of conjugated dienes that may be used include 1,3-butadiene, isoprene, 1,3-pentadiene, and 1,3-hexadiene. Preferably the conjugated diene is unsubstituted and preferably the conjugated diene only contains carbon atoms. Most preferably, the conjugated diene is 1,3-butadiene.

In the telomerization process of 1,3-butadiene, 1-substituted-2,7-octadiene can be prepared. 1-substituted-2,7-octadiene can be useful in a process to prepare 1-octene containing substantially no branched olefinic $C_8$-isomers. Therefore, a process for the preparation of 1-octene is provided, comprising:

a) telomerization of 1,3-butadiene as described herein, to form 1-substituted-2,7-octadiene;
b) hydrogenation of the 1-substituted-2,7-octadiene of step a) to form 1-substituted octane;
c) decomposition of the 1-substituted octane of step b) to form 1-octene.

Step a) of this process can be carried out as described herein. Steps b) and c) can be conveniently carried out as described in WO-A-9210450.

The conjugated diene used as a starting compound may contain small amounts of other saturated or unsaturated hydrocarbons. For example, a crude $C_4$ hydrocarbon mixture may be used as a feed for 1,3-butadiene. Such a crude $C_4$ mixture may contain, besides 1,3-butadiene other $C_4$-hydrocarbons such as butenes and butanes.

The active hydrogen-containing compound R'—H may be any compound having a reactive hydrogen atom. Examples of such active hydrogen-containing compounds include alkanols, hydroxy-aromatic compounds, carboxylic acids, ammonia, primary and secondary amines and water.

Preferred active hydrogen-containing compounds include water, alkanols and hydroxy-aromatic compounds.

Alkanols that can be used in the process of the invention include mono- or poly alkanols, which can be linear or branched and saturated or unsaturated. Preferred alkanols for the process of the invention are alkanols with from 1 to 20, more preferably with from 1 to 6 carbon atoms per molecule and alkanediols with from 2 to 20, more preferably from 2 to 6 carbon atoms per molecule. Suitable alkanols in the process of the invention include methanol, ethanol, ethanediol, propanol, 1,2-propanediol, 1,3-propanediol, iso-propanol, butanol, 1,2-butanediol, 1,4-butanediol, iso-butanol, tert-butanol, pentanol, hexanol, hexanediol, cyclohexanol, and cyclohexanediol. Of these, methanol, ethanol and phenol are preferred. Methanol and phenol are especially preferred.

Examples of hydroxy-aromatic compounds are aromatic compounds containing one or more rings such as phenol, benzylalcohol, cresols, xylenols, naphthol as well as polyhydric compounds such as resorcinol, hydroquinone and pyrocatechol. Also alkyl-, alkoxy- and/or halogen-substituted aromatic hydroxy compounds may be used.

Examples of carboxylic acids that may be used in the process of the invention include aliphatic carboxylic acids with up to about 20 carbon atoms. Preferred carboxylic acids are those having from 1 to 6 carbon atoms such as e.g. acetic acid, propionic acid, butyric acid. Examples of suitable aromatic carboxylic acids include benzoic acid and toluene carboxylic acid. Also carboxylic diacids can be used, such as for example adipic acid and phthalic acid.

Examples of amine compounds that can be used in the process according to the invention are ammonia and primary and secondary amines. Suitable amine compounds include for example primary aliphatic amines, such as methylamine, ethylamine, butylamine, dodecylamine and the like; primary aromatic amines, such as aniline, toluidine, benzylamine and the like; secondary amines such as dimethylamine, diethylamine, N-methylaniline, dicyclohexylamine, methylhexylamine, and the like; as well as polyamine such as phenylenediamine, ethylene-diamine; and heterocyclic amines, such as piperidine.

The telomerization reaction is carried out in the presence of certain catalysts.

The group VIII metal is preferably selected from the metals rhodium, nickel, palladium and platinum. Of these, palladium and platinum are preferred. Palladium is most preferred.

Examples of suitable metal sources are metallic platinum or palladium and platinum or palladium on a carrier. Other suitable sources include, for example, platinum or palladium cation complexes which are converted into Pd (0) or Pt (0) during the reaction. Examples of such platinum or palladium cation complexes include carboxylates of platinum or palladium. A preferred source of palladium is tetrakis(dibenzylacetone) palladium.

The bidentate ligand has the general formula I

$$R^1R^2M^1\text{-}R\text{-}M^2R^3R^4 \tag{I}$$

wherein $M^1$ and $M^2$ are independently P, As or Sb;
$R^1$, $R^2$, $R^3$ and $R^4$ independently represent a monovalent aliphatic group;
or $R^1$, $R^2$ and $M^1$ together and/or $R^3$, $R^4$ and $M^2$ together independently represent an optionally substituted aliphatic cyclic group with at least 5 ring atoms, of which one is the $M^1$ or $M^2$ atom, respectively;
and R represents a bivalent organic bridging group.

In the bidentate ligand of formula I, $M^1$ and $M^2$ are preferably the same and more preferably they both represent phosphorus atoms.

The bivalent organic bridging group R preferably has from 1 to 6 and more preferably from 2 to 6 atoms in the bridge. By "in the bridge" as used herein is understood to mean the shortest connection between the atoms $M^1$ and $M^2$.

Suitable bridging groups include substituted and unsubstituted alkylene groups. The alkylene group can contain one or more hetero-atoms, such as Si, N, O, S, in the bridge, but preferably has only carbon atoms in the bridge. The alkylene group can be substituted with one or more groups, and is preferably substituted with two groups. The substituents can contain one or more hetero-atoms. Examples of unsubstituted alkylene bridging groups include methylene, ethylene and tri-methylene groups. Examples of substituted alkylene bridging groups include for example 2,2-dimethyl-trimethylene (i.e. neopentylene), 2,2-diethyl-trimethylene, 2,2-dimethyl-tetramethylene, 2-methyl,2-hydroxymethyl-trimethylene (i.e. neopentylol), 2,2 di-hydroxymethyl-trimethylene (i.e. neopentyldiol). Preferred alkylene bridging groups are ethylene, trimethylene and neopentylene groups, preferably connecting respectively the $M^1$ and $M^2$ atom by the first and the second or the third carbon atom, such as, for example, a 1,2-ethylene, a 1,3-trimethylene or a 1,3-neopentylene group. Of these, neopentylene groups are especially preferred. Preferably the neopentylene bridging group is substituted with one or more hydroxy groups.

The bridging group can also comprise one or more aliphatic or aromatic ring structures. Preferably such a bridging group still contains only from 2 to 6 carbon atoms in the bridge. An especially preferred bridging group contains two aromatic ring structures, preferably two benzene rings. These aromatic ring structures are preferably connected to each other and to two alkylene groups which in their turn are connected to respectively $M^1$ and $M^2$.

The alkylene groups are preferably connected to the aromatic ring structures at their ortho positions vis-à-vis the carbon atoms through which the aromatic ring structures are connected.

In a preferred embodiment $R^1$, $R^2$, $R^3$ and $R^4$ independently represent a primary, secondary or tertiary alkyl group. Preferably the alkyl group has from 1 to 10 carbon atoms, more preferably from 1 to 6 carbon atoms. Examples of such alkyl groups include methyl, ethyl, propyl, isopropyl, butyl, sec-butyl, iso-butyl, tert-butyl, pentyl, sec-pentyl, cyclopentyl, hexyl, cyclohexyl. Preferably $R^1$, $R^2$, $R^3$ and $R^4$ independently represent a primary alkyl group. Examples of suitable primary alkyl groups include methyl, ethyl and propyl. Preferably the groups R¹ to R⁴ represent the same primary alkyl groups, most preferably R¹ to R⁴ are methyl or ethyl groups.

In a further preferred embodiment R¹, R² and M¹ together and/or R³, R⁴ and M² together independently represent an optionally substituted aliphatic cyclic group with at least 5 ring atoms, of which one is the M¹ or M² atom, respectively.

By "a cyclic group" is understood a monocyclic or a polycyclic group such as bicyclic or tricyclic groups. Preferred cyclic groups are bicyclic groups. The cyclic group contains at least one hetero-atom, i.e. the M¹ or M² atom, respectively, but can contain more hetero-atoms. Suitable hetero-atoms that can further be present in the cyclic group include P, As, Sb, O, N, S and Si. The optionally substituted aliphatic cyclic group contains at least 5 ring atoms. Preferably the cyclic group contains from 6 to 20 ring atoms, more preferably from 6 to 12 ring atoms.

Preferably M¹ and M² are both phosphorus and R¹, R² and M¹ together and R³, R⁴ and M² together both represent a phosphabicycloalkyl group. In a highly preferred embodiment the aliphatic cyclic group contains 9 ring atoms and forms a 9-phosphabicyclononyl group. The 9-phosphabicyclononyl group can have several isomeric structures. For the purpose of the invention the [3,3,1] and [4,2,1] isomers are preferred. R¹, R² and M¹ together and/or R³, R⁴ and M² together can both have the same or each have a different isomeric structure. Preferably both R¹, R² and M¹ together and/or R³, R⁴ and M² together have the [3,3,1] structure.

One or both of the phosphabicycloalkyl rings may be substituted with one or more suitable hydrocarbyl groups containing carbon atoms and/or hetero-atoms. Suitable substituents include groups containing hetero-atoms such as halides, sulphur, phosphorus, oxygen and nitrogen. Examples of such groups include chloride, bromide, iodide, thiol, and groups of the general formula —Y¹—OH, —Y¹—CO—OH, —Y¹—SH, —S—Y¹, —O—Y¹, —CO—Y¹, —NH₂, —NHY¹, —NY¹Y², —CO—NY¹Y², —OH, —PO₄, —NO₂, —NOH, —CO, —SO₂, —S—OH, in which Y¹ and Y², independently, represent C₁-C₁₀ alkyl groups. If a phosphabicycloalkyl ring is substituted it is preferably substituted with a carbon containing group. Such a carbon containing group may, however, contain additional hetero-atoms, such as halides, sulphur, oxygen and nitrogen or hetero-groups as described hereinbefore. Preferably, substituted phosphabicycloalkyl rings are substituted with alkyl groups, preferably having from 1 to 10 carbon atoms, more preferably from 1 to 4 carbon atoms. Linear, branched or cyclic alkyl groups can be used. Suitable alkyl groups include, methyl, ethyl, propyl, iso-propyl, butyl and iso-butyl. More suitably methyl groups are used. If the phosphabicycloalkyl ring is substituted, it may be mono- or poly-substituted and is preferably di-substituted. More preferably the phosphabicycloalkyl ring in this case is substituted with two methyl groups. The phosphabicycloalkyl ring may be substituted at all carbon atoms of the ring. However, the use of rings with substituents on certain carbon atoms may be more beneficial. Suitably, phosphabicyclononyl rings can be used with substituents on two carbon atoms, suitably carbon atom 1, 2, 8 and carbon atom 4, 5 or 6.

Examples of preferred bidentate ligands include
1,3-bis(diethylphosphino)-propane;
1,3-bis(dimethylphosphino)-propane;
1,3-bis-(1,4-cyclooctylene-phosphino)-propane, i.e. 1,3-PP'bis(9-phosphabicyclo[4,2,1]nonyl)-propane;
1,3-bis-(1,5-cyclooctylene-phosphino)-propane, i.e. 1,3-PP'bis(9-phosphabicyclo[3,3,1]nonyl)-propane;
1,2-bis-(1,4-cyclooctylene-phosphino)-ethane, i.e. 1,2-PP'bis(9-phosphabicyclo[4,2,1]nonyl)-ethane;
1,2-bis-(1,5-cyclooctylene-phosphino)-ethane, i.e. 1,2-PP'bis(9-phosphabicyclo[3,3,1]nonyl)-ethane;
2,2-dimethyl, 1,3-PP'bis(9-phosphabicyclo-[3,3,1]nonyl)-propane;
2-methyl, 2-hydroxymethyl, 1,3-PP'bis(9-phospha-bicyclo[3,3,1]nonyl)-propane;
2,2-dimethyl, 1,3-PP'bis(9-phosphabicyclo-[4,2,1]nonyl)-propane;
2-methyl, 2-hydroxymethyl, 1,3-PP'bis(9-phospha-bicyclo[4,2,1]nonyl)-propane;
2,2'-bis-(1,4-cyclooctylene-phosphino-methyl)-1,1'-biphenyl;
2,2'-bis-(1,5-cyclooctylene-phosphino-methyl)-1,1'-biphenyl;
and mixtures thereof.

Some of the bidentate ligands that can be used in the present invention are considered to be novel.

The present invention therefore also relates to a bidentate ligand of formula II,

R¹R²M¹-V-M²R³R⁴ (II)

wherein M¹ and M² are independently P, As or Sb;
R¹, R², R³ and R⁴ independently represent a monovalent aliphatic group;
or R¹, R² and M¹ together and/or R³, R⁴ and M² together independently represent an optionally substituted aliphatic cyclic group with at least 5 ring atoms, of which one is the M¹ or M² atom, respectively;
and V represents a bridging group comprising a trimethylene group connecting M¹ and M² of which the middle carbon atom has two additional bondings with a non-hydrogen atom.

R¹,R²,M¹,M²,R³ and R⁴ represent the same groups as described hereinbefore. Preferences are as described hereinbefore.

V represents a bridging group comprising a tri-methylene group connecting M¹ or M² of which the middle carbon atom has two additional bondings with a non-hydrogen atom. The middle carbon atom can have two additional bondings with one non-hydrogen atom, i.e. a double bond, or it can have two additional bondings with two separate non-hydrogen atoms.

Examples of non-hydrogen atoms to which the middle carbon group can be double bonded include hetero-atoms, such as oxygen, nitrogen, sulphur or silicon. Furthermore the middle carbon atom can be double bonded to another carbon atom.

Preferably, however, the middle carbon has two additional bondings with two separate non-hydrogen atoms. In a preferred embodiment the bridging group V represents a group having the formula

—C(V1)-C(V3,V4)-C(V2)- (IV)

wherein V1 and V2 independently represent an optionally substituted alkyl group having from 1 to 4 carbon atoms, such as methyl, ethyl, propyl and isopropyl, or hydrogen; and V3 and V4 independently represent a non-hydrogen group.

V3 and V4 each can represent a separate group, or V3, V4 and the middle carbon atom together can form a cyclic group.

If V3, V4 and the middle carbon atom together form a cyclic group, the cyclic group preferably comprises from 3 to 10 ring atoms, more preferably from 3 to 6 ring atoms. The ring atoms can be hetero-atoms or carbon atoms but are preferably carbon atoms.

Preferably, however, V3 and V4 each independently represent a separate hydrocarbyl group containing carbon atoms and/or hetero-atoms. Suitable hydrocarbyl groups for this purpose include groups containing hetero-atoms such as sulphur, phosphorus, oxygen and nitrogen. Examples of such groups include groups of the general formula —$X^1$—OH, —$X^1$—CO—OH, —$X^1$—SH, —S—$X^1$, —O—$X^1$, —CO—$X^1$, —$NH_2$, —$NHX^1$, —$NX^1X^2$, —CO—$NX^1X^2$, —OH, —$PO_4$, —$NO_2$, —NOH, —CO, —$SO_2$, —S—OH, in which $X^1$ and $X^2$, independently, represent alkyl or alkylene groups having from 1 to 10 carbon atoms. Preferably V3 and/or V4 represent a carbon containing group. Such a carbon containing group may, however, contain additional hetero-atoms such as halides, sulphur, oxygen and nitrogen or hetero groups as described hereinbefore. Preferably V3 and/or V4 represent groups chosen from methyl, ethyl, propyl, hydroxymethyl and hydroxyethyl.

Preferred bidentate diphosphines according to formula II include 2,2-dimethyl-1,3-bis-(1,4-cyclooctylene-phosphino)-propane;
2-methyl-2-hydroxymethyl-1,3-bis-(1,4-cyclooctylene-phosphino)-propane;
2,2-dihydroxymethyl-1,3-bis-(1,4-cyclooctylene-phosphino)-propane;
2,2-dimethyl-1,3-bis-(1,5-cyclooctylene-phosphino)-propane;
2-methyl-2-hydroxymethyl-1,3-bis-(1,5-cyclooctylene-phosphino)-propane;
2,2-dihydroxymethyl-1,3-bis-(1,5-cyclooctylene-phosphino)-propane.

These ligands can be prepared by:
i) reacting P-cyclo-octylene hydride (phosphabicyclononane hydride) and butyllithium to generate a lithium cyclo-octylene phosphide (lithiated phosphabicyclononane).
ii) introducing a tosylate group to 3-methyl-3-oxetane methanol by reaction with p-toluene sulfonyl chloride in dichloromethane as solvent at 0° C. in the presence of pyridine.
iii) reacting the phosphide of step i) with the tosylate substituted oxetane of step ii), at for example 0° C. for the first phosphide group and reflux conditions for the second phosphide group, in for example tetrahydrofuran as a solvent. An illustration of this reaction is given in FIG. 1.

The present invention further relates to a bidentate ligand of formula (III),

wherein $M^1$ and $M^2$ are independently P, As or Sb;
$Q^1$, $Q^2$ and $M^1$ together and $Q^3$, $Q^4$ and $M^2$ together independently represent an optionally substituted aliphatic cyclic group with at least 5 ring atoms, of which one is the $M^1$ or $M^2$ atom, respectively;
$Q^5$ and $Q^6$ each independently represent optionally substituted alkylene groups;
and $Ar^1$ and $Ar^2$ independently represent an optionally substituted aromatic group.

$M^1$ and $M^2$ represent the same groups as described hereinbefore. Preferences are as described hereinbefore.

$Q^1$, $Q^2$ and $M^1$ together and $Q^3$, $Q^4$ and $M^2$ together independently represent an optionally substituted cyclic group with at least 5 ring atoms, of which one is the $M^1$ or $M^2$ atom, respectively. Preferences are the same as for the cyclic groups represented by $R^1$, $R^2$ and $M^1$ together, and $R^3$, $R^4$ and $M^2$ together, respectively as described hereinbefore.

$Q^5$ and $Q^6$ each independently represent an optionally substituted alkylene group. Preferably this alkylene group contains from 1 to 6, more preferably from 1 to 4 carbon atoms. The alkylene group can be substituted with one or more hydrocarbyl groups. If the alkylene group is substituted, it is preferably substituted with alkyl groups, preferably having from 1 to 6, more preferably from 1 to 4 carbon atoms.

Preferably the alkylene group is unsubstituted. Preferably both alkylene groups are the same and preferably both alkylene groups are unsubstituted methylene or ethylene groups. Most preferably both $Q^5$ and $Q^6$ represent an unsubstituted methylene group.

$Ar^1$ and $Ar^2$ each independently represent an aromatic group. Preferably the aromatic group contains from 6 to 20 carbon atoms, more preferably from 6 to 14 carbon atoms. Examples of suitable aromatic groups include phenyl, naphthyl, phenanthryl and anthracenyl. Of these, phenyl groups are preferred. The aromatic group can be substituted with one or more hetero-atoms and/or hydrocarbyl groups. Hydrocarbyl groups used for this purpose include alkyl, alkoxy and carbonyl groups. Preferably the aromatic group is unsubstituted. The aromatic groups are preferably connected with each other by the carbon atom next to the carbon atom attached to the alkylene group.

Preferred bidentate diphosphine according to formula III include
2,2'-bis-(1,4-cyclooctylene-phosphino-methyl)-1,1'-biphenyl;
2,2'-bis-(1,5-cyclooctylene-phosphino-methyl)-1,1'-biphenyl, and mixtures thereof.

These ligands can be prepared by reacting P-cyclo-octylene hydride (phosphabicyclononane hydride) and butyllithium to generate a lithium cyclo-octylene phosphide (lithiated phosphabicyclononane). The latter phosphide is reacted with a 2,2'-dimethyl-1,1'biphenyl group substituted with suitable leaving groups, preferably tosylates, mesylates and triflates, in an appropriate manner. Preferred aliphatic groups are those having a cyclic sulphate structure as a leaving group, such as cyclic substituted or unsubstituted alkane diol sulphate esters, also called cyclic alkyl sulphates.

For example 2,2'-bis-(1,4-cyclooctylene-phosphino-methyl)-1,1'-biphenyl can be prepared by reacting phosphabicyclononane hydride and butyllithium to generate the corresponding lithium phosphide and subsequently reacting this lithium phosphide, at for example 0° C. in tetrahydrofuran, with the di-p-tosylate ester of 2,2'-dimethyl-1,1'biphenyl wherein the tosylate groups are substituted on the methyl groups.

The P-cyclo-octylene hydride (phosphabicyclononane hydride) may conveniently be prepared as described by Elsner et al. (Chem. Abstr. 1978, vol. 89, 180154x).

The present invention further provides a catalyst system comprising:
I) a source of group VIII metal;
II) a bidentate ligand according to the general formula II or III as described hereinbefore.

The catalyst system can be advantageously used for the telomerization of conjugated dienes.

The amount of telomerization catalyst to be used is not critical, and any catalytically effective amount may be used. In general, amounts between about 0.000001 and about 1, and preferably between about 0.000005 and about 0.01 gram atom of Group VIII metal per mole of conjugated diene can be used. In order to achieve high catalyst efficiencies without having to recycle the catalyst, amounts of less than 0.0001, preferably less than 0.00005, and more preferably less than 0.00002 gram atoms of Group VIII metal are used per mole of conjugated diene.

The bidentate ligand is generally used in a relative amount of from about 1 to about 20 moles, and preferably from about 2 to about 15 moles of bidentate ligand per gram atom of the Group VIII metal. The bidentate ligand can be added as a separate compound to the reaction mixture or zone or to a catalyst make-up solution, or it may be incorporated in a Group VIII metal complex.

Preferably, the process according to the present invention can be conducted in the substantial absence of oxygen, as oxygen reacts with the bidentate ligand and consequently may result in decreased catalyst activity.

In the process, one or more of the reactants and/or the formed product may act as reaction diluent. The reaction may also be carried out in the additional presence of a solvent. As such, saturated hydrocarbons, e.g. paraffins and isoalkanes are preferred. Further suitable solvents include, for example, ethers such as 2,5,8-trioxanonane (diglyme), diethylether and anisole, and ketones, such as methylbutylketone. Solvents, comprising or substantially consisting of sulphones are also preferred. Sulphones are in particular preferred, for example dialkylsulphones such as dimethylsulphone and diethylsulphone and cyclic sulphones, such as sulfolane (tetrahydrothiophene-2,2-dioxide), sulfolane, 2-methyl-sulfolane and 2-methyl-4-ethylsulfolane.

The temperature at which the telomerization reaction is carried out is not critical. Normally, temperatures within the range of ambient temperature to about 150° C. can be used. Preferably, the reaction temperature is within the range of from about 40 to about 100° C. and more preferably from about 50 to about 100° C.

The pressure at which the telomerization reaction is carried out is not critical. Generally the reaction pressure is within the range of between about 1 and about 10 bars.

The telomerization reaction can be carried out continuously, semi-batch or batch-wise.

In general, any conventional hydrogenation process can be used in preparing 1-octene. The hydrogenation may be carried out in the liquid phase or in the vapor phase.

Depending on the nature of the starting material, the reaction can be carried out at a temperature between 0 and 400° C. Preferably the temperature is in the range from ambient to 350° C. More preferably the hydrogenation is carried out at a temperature between 50 and 200° C. The pressure is not critical and depends on whether the hydrogenation is carried out in the liquid or vapor phase. In general the pressure can vary between 0.1 and 100 bar.

In process step (b) any of the conventional homogeneous and heterogeneous hydrogenation catalysts can be used. Examples of such catalysts include the Group VIII of the periodic system transition metal catalysts. Preferred catalysts are the noble metal catalysts of this group VIII, either in elemental form or in the form of a compound which is reducible by hydrogen under hydrogenation conditions to form-f-inely divided elemental metal, or mixtures thereof. Examples of such compounds are the oxides, halides, nitrates, oxalates, acetates, carbamates, propionates, tartrates, hydroxides and the like or mixtures thereof. Preferred catalysts are palladium and platinum, whereas also Raney-nickel may advantageously be used. These catalysts may be modified with other metals. The catalysts may preferably be supported on a carrier material, such as for example active carbon, alumina, silica, silica-alumina, calcium carbonate, barium carbonate, barium sulfate, clays, Kieselguhr and the like. Particularly preferred catalysts are alumina supported platinum or palladium catalysts, the metal preferably being dispersed on the support in an amount of 0.1 to 1.0 wtX.

The hydrogenation catalysts are used in the amounts conventional for these type of reactions and catalysts.

Generally, the relative amounts of hydrogen, in the form of pure hydrogen or as a hydrogen containing gas, and the 1-substituted-2,7-octadiene are not critical, but it is preferred to use a molar ratio between hydrogen and the 1-substituted-2,7-octadiene in the range from 2:1 to 50:1, more preferably from 2:1 to 10:1.

The hydrogenation can advantageously be carried out in a diluent or solvent for dilution of the material to be hydrogenated. The usual diluents may be used for this, such as saturated hydrocarbons having 4 to 12 carbon atoms, alkanols containing from 1 to 12 carbon atoms, acyclic and cyclic ethers having 4 to 12 carbon atoms-and mixtures thereof. Advantageously, part of the reaction product of the hydrogenation reaction is recycled to step (b) and used as diluent in the hydrogenation reaction.

The hydrogenation in step (b) can be carried out according to batch, semi-continuous or continuous procedures. It may also be performed in more than one step, such as for example in a preliminary hydrogenation step and a finishing hydrogenation step. Typical weight hourly space velocities (based on reactant) are in the range of 0.1-50, preferably in the range of 0.2-10 and more preferably in the range of 0.5-5.

In the decomposition process step (c), of the present invention any suitable conventional catalyst can be used which is capable of decomposing the 1-substituted octane to give 1-octene. Generally, a solid acidic catalyst is used for this purpose. Preferably an alumina catalyst is used. Examples of such catalysts are alpha, delta, gamma, etha and theta-aluminas, which may be modified with metal-containing weakly acidic components, organic carboxylic acids, or other treating agents.

The temperatures at which the decomposition process is carried out depend on the decomposition temperature of the respective compound and on the catalyst activity. Generally the temperatures are up to 500° C., preferably in the range of 200 to 400° C., whereas temperatures in the range of 250 to 350° C. are more preferred.

The pressure under which the decomposition reaction may be carried out is not critical and can vary widely, for example from 0.1 to about 50 bar.

Preferably the reaction is carried out at a pressure between 0.2 and 10 bar.

The reaction can be carried out in the vapor or in the liquid phase, the vapor phase being preferred.

An inert carrier gas or an inert diluent may be used to dilute the reactant. Examples of such inert gases are nitrogen, helium, argon and the like or mixtures thereof.

The reaction may be carried out continuously, semi-continuously or batchwise. In the continuous mode the reactant(s) and possibly the diluent are continuously passed over a bed of the catalyst at the desired reaction conditions. The reactant is generally added to the reactor containing the catalyst under the desired reaction conditions at a weight hourly space velocity of about 0.01 to about 50, and preferably about 0.1 to about 10.

The desired product 1-octene may be recovered from the reaction mixture using conventional methods such as solvent extraction, (fractional) distillation, (fractional) condensation etc.

ture was maintained during the reaction time as specified in Table I. Thereafter the autoclave was cooled to room temperature and the contents were analyzed by standard GLC. The obtained reaction rate and selectivity towards the linear 1-substituted 2,7-octadiene are given in Table I. Generated by-products included vinylcyclo-hexene and mono-butenyl ethers.

The mono-butenyl ethers can be very useful in a wide range of other applications. The reaction rate is defined as the average rate over 90% butadiene conversion.

TABLE I

| Example | Medium | Bidentate ligand | Temperature | Reaction time (hours) | Reaction rate (mol/mol/hr) | Selectivity towards linear telomerization product |
|---|---|---|---|---|---|---|
| 1 | 20 ml methanol/ 40 ml diglyme | BDEPP | 70 | 0.5 | 1400 | 91.5 |
| 2 | 20 ml methanol/ 40 ml NMP | BDEPP | 70 | 0.5 | 1000 | 90 |
| 3 | 20 ml methanol/ 40 ml diglyme | BDMPP | 70 | 0.25 | 2000 | 94 |
| 4 | 20 ml methanol/ 40 ml diglyme | BCOPP | 70 | 1.5 | 500 | 93 |
| 5 | 50 ml methanol | MHBCOPP | 70 | 0.25 | 3000 | 95 |
| 6 | 50 ml methanol | BCOPE | 70 | 0.25 | 2000 | 94 |
| 7 | 50 g phenol/ 40 ml diglyme | BCOPE | 60 | 0.5 | 1500 | 90 |
| 8 | 50 ml methanol | 1,4 BCOPMB | 70 increased to 85 | n.d. | n.d. | 96[1] |
| 9 | 50 ml methanol | 1,5 BCOPMB | 70 | n.d. | n.d. | 92[2] |
| A | 50 ml methanol | DPPP | 70 | 5 | n.d. | —[3] | n.d. = not determined
BDEPP = 1,3-bis(diethylphosphino)-propane
BDMPP = 1,3-bis(dimethylphosphino)-propane
BCOPP = mixture of 1,3-bis (1,4-cyclo-octylenephosphino) propane and 1,3-bis (1,5-cyclo-octylenephosphino) propane
BCOPE = mixture of 1,2-bis (1,4-cyclo-octylenephosphino) ethane and 1,2-bis (1,5-cyclo-octylenephosphino) ethane
MHBCOPP = 2-methyl, 2-hydroxymethyl, 1,3-bis (1,4-cyclo-octylenephosphino) propane
1,4 BCOPMB = 2,2'-bis-(1,4-cyclooctylene-phosphino-methyl)-1,1'-biphenyl
1,5 BCOPMB = 2,2'-bis-(1,5-cyclooctylene-phosphino-methyl)-1,1'-biphenyl
NMP = N-methyl-2-pyrrolidone
DPPP = 1,3-bis(diphenylphosphino)-propane
[1] = only 4% telomerization product was formed, whereas 59% mono-butenyl ethers were formed
[2] = only 31% telomerization product was formed, whereas 59% mono-butenyl ethers were formed
[3] = only traces of ethers were formed The invention will be illustrated by the following non-limiting examples.

EXAMPLES 1-9 AND COMPARATIVE EXAMPLE A

The experiments were carried out in a 250 ml Hastelloy C autoclave. The telomerization catalyst was prepared separately as a 5 ml methanol solution of 0.25 mmol Pd(dibenzylacetone)$_2$ and 0.3 mmol bidentate ligand as given in Table I. The catalyst solution was introduced under a nitrogen atmosphere to a medium of alkanol and optionally additional inert solvent in the autoclave as indicated in Table I. The autoclave was closed, evacuated and 15 ml 1,3 butadiene was pumped in.

Subsequently, the reactor was sealed and the contents were heated to a temperature as specified in Table I. The tempera-

The invention claimed is:
1. A catalyst system comprising
   I) a source of group VIII metal;
   II) a bidentate ligand which is selected from the group consisting of 2,2-dimethyl-1,3-bis-(1,4-cyclooctylene-phosphino)-propane, 2-methyl-2-hydroxymethyl-1,3-bis-(1,4-cyclooctylene-phosphino)-propane; 2,2 dihydroxymethyl-1,3-bis-(1,4-cyclooctylene-phosphino)-propane; 2,2-dimethyl-1,3-bis-(1,5-cyclooctylene-phosphino)-propane; 2-methyl-2-hydroxymethyl-1,3-bis-(1,5-cyclooctylene-phosphino)-propane; and 2,2 dihydroxymethyl-1,3-bis-(1,5-cyclooctylene-phosphino)-propane.

* * * * *